(12) United States Patent
Meriaux et al.

(10) Patent No.: US 9,810,612 B2
(45) Date of Patent: Nov. 7, 2017

(54) OLIGOCYCLIC FATIGUE OR OLIGOCYCLIC AND POLYCYCLIC FATIGUE TEST RIG

(71) Applicants: SNECMA, Paris (FR); TURBOMECA, Bordes (FR)

(72) Inventors: Jean Vincent Manuel Meriaux, Moissy-Cramayel (FR); Guillaume Puech, Moissy-Cramayel (FR); Juan-Antonio Ruiz-Sabariego, Moissy-Cramayel (FR); Nathalie Serres, Moissy-Cramayel (FR); Laurent Houze, Andoins (FR)

(73) Assignees: SNECMA, Paris (FR); TURBOMECA, Bordes (FR)

( * ) Notice: Subject to any disclaimer, the term of this patent is extended or adjusted under 35 U.S.C. 154(b) by 48 days.

(21) Appl. No.: 14/891,281

(22) PCT Filed: May 9, 2014

(86) PCT No.: PCT/FR2014/051072
§ 371 (c)(1),
(2) Date: Nov. 13, 2015

(87) PCT Pub. No.: WO2014/184468
PCT Pub. Date: Nov. 20, 2014

(65) Prior Publication Data
US 2016/0084744 A1    Mar. 24, 2016

(30) Foreign Application Priority Data

May 17, 2013 (FR) ..................... 13 54435

(51) Int. Cl.
*G01N 3/00* (2006.01)
*G01N 3/02* (2006.01)
(Continued)

(52) U.S. Cl.
CPC .............. *G01N 3/02* (2013.01); *G01M 7/027* (2013.01); *G01M 15/14* (2013.01); *G01N 3/04* (2013.01);
(Continued)

(58) Field of Classification Search
CPC .... G01N 3/02; G01N 3/32; G01N 2203/0008; G01N 2203/0005; G01N 2203/0423;
(Continued)

(56) References Cited

U.S. PATENT DOCUMENTS 2,419,711 A    4/1947  Dillon
5,606,168 A    2/1997  Chiron
(Continued)

FOREIGN PATENT DOCUMENTS

FR    2963425 A1    2/2012
GB     228625 A     2/1925

OTHER PUBLICATIONS

International Search Report dated Jul. 11, 2014, issued in corresponding International Application No. PCT/FR2014/051072, filed May 9, 2014, 3 pages.
(Continued)

*Primary Examiner* — Harshad R Patel
*Assistant Examiner* — Brandi Hopkins
(74) *Attorney, Agent, or Firm* — Christensen O'Connor Johnson Kindness PLLC

(57) ABSTRACT

A low-cycle fatigue test rig reproduces bearing of turbine engine parts. The test rig includes a support member that is fixed to a frame and defines at least one bearing surface. A test piece is connected to a traction element for loading the test piece so that the test piece bears against the at least one bearing surface of the support member. The at least one bearing surface is supported by a support element that is mounted to rotate about a first axis on the support member.
(Continued)

The test piece is connected to the traction element for articulation around a second axis that is perpendicular to the first axis. The test rig is configured to enable adjusting and locking the support element and the test piece in positions around the above-mentioned axes.

10 Claims, 3 Drawing Sheets

(51) Int. Cl.
　　　*G01N 3/04*　　　(2006.01)
　　　*G01N 3/32*　　　(2006.01)
　　　*G01M 7/02*　　　(2006.01)
　　　*G01M 15/14*　　(2006.01)
(52) U.S. Cl.
　　　CPC ....... *G01N 3/32* (2013.01); *G01N 2203/0005* (2013.01); *G01N 2203/0008* (2013.01); *G01N 2203/0423* (2013.01)
(58) Field of Classification Search
　　　CPC ............. G01N 3/04; G01N 2203/0226; G01N 2203/0435; G01N 2203/0246; G01N 2203/0035; G01N 2203/0066; G01N 2203/0623; G01N 2203/0023; G01N 2203/0064; G01N 2203/0073; G01N 2203/0441; G01N 3/38; G01N 2203/0051; G01N 2203/0641; G01N 2203/0016; G01M 15/14; G01M 7/027; G01M 5/005; G01M 5/0016
　　　USPC ......... 73/788, 862–863, 808, 856, 831, 806, 73/662, 794, 810, 813, 815, 821
　　　See application file for complete search history.

(56) References Cited

U.S. PATENT DOCUMENTS

| | | |
|---|---|---|
| 6,033,185 A | 3/2000 | Lammas |
| 6,250,166 B1 | 6/2001 | Dingwell |
| 2002/0017144 A1 | 2/2002 | Miles |
| 2010/0263453 A1 | 10/2010 | Mason |
| 2011/0000308 A1 | 1/2011 | Bassot et al. |

OTHER PUBLICATIONS

Written Opinion of the International Searching Authority dated Jul. 11, 2014, issued in corresponding International Application No. PCT/FR2014/051072, filed May 9, 2014, 6 pages.
International Preliminary Report on Patentability dated Nov. 17, 2015, issued in corresponding International Application No. PCT/FR2014/051072, filed May 9, 2014, 1 page.

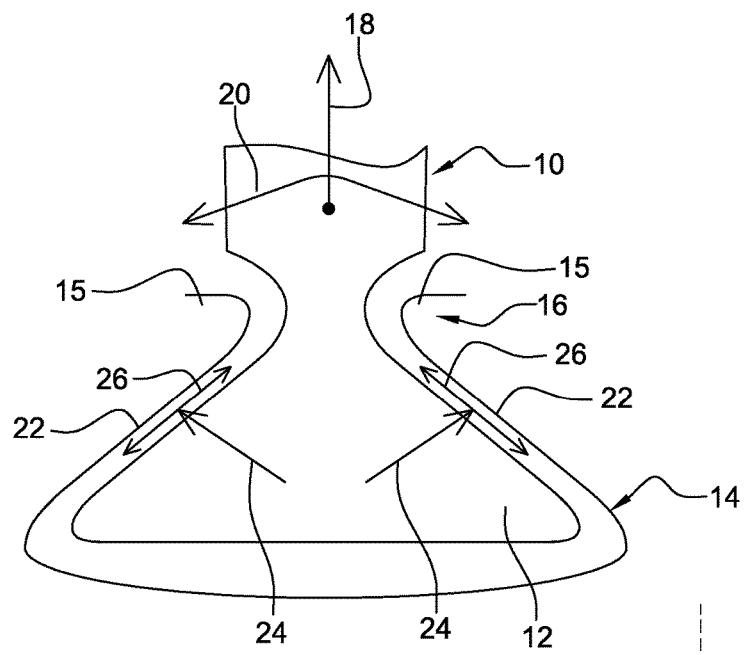
Fig. 1
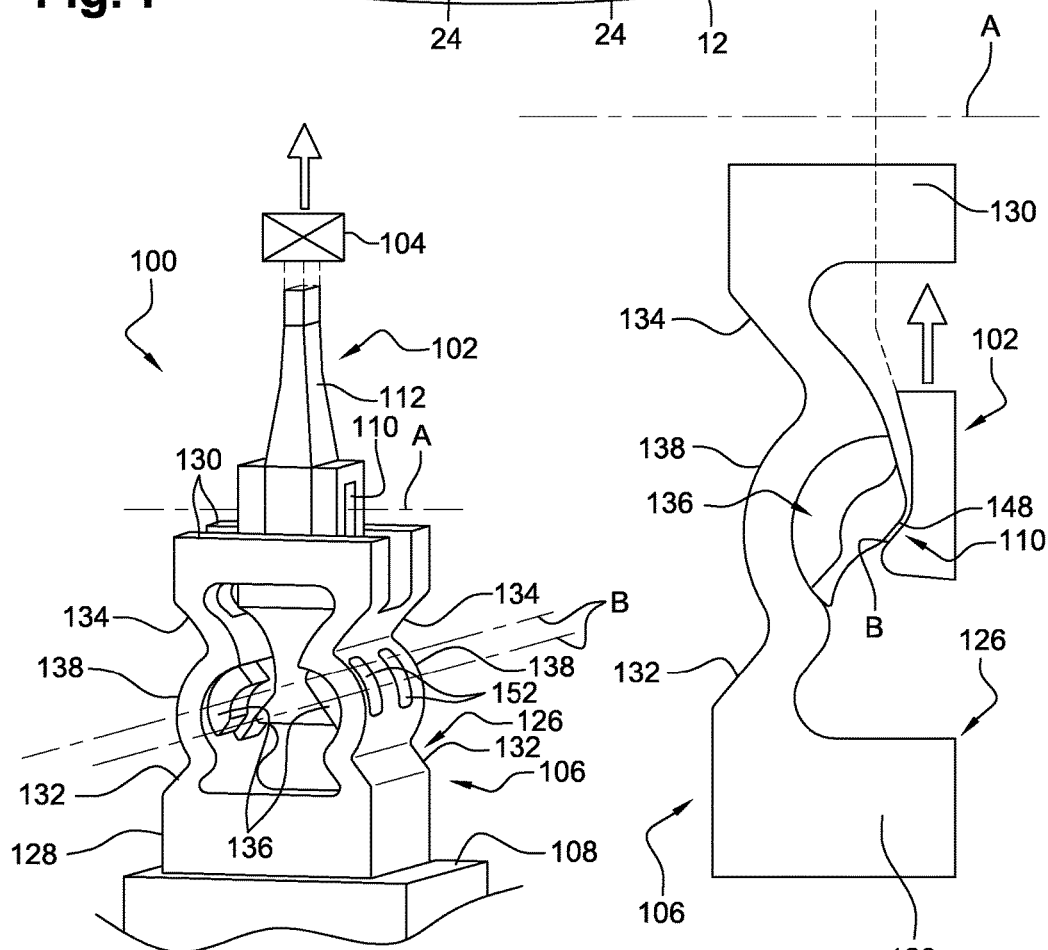
Fig. 2
Fig. 3

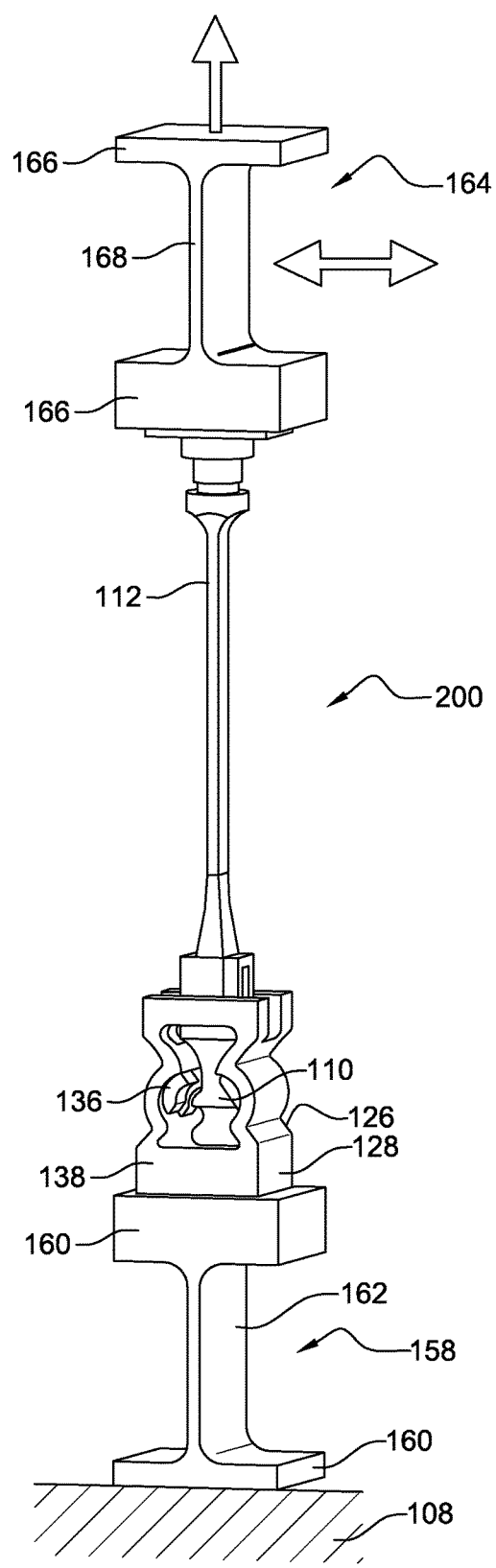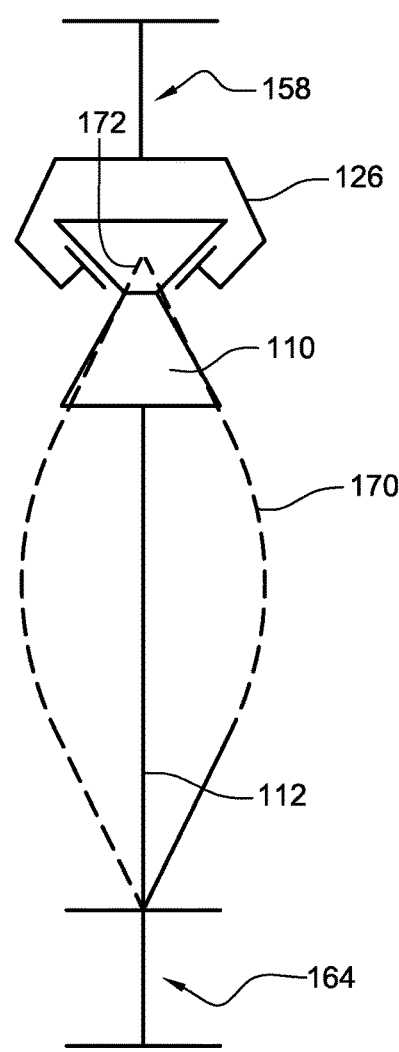
Fig. 8
Fig. 9

OLIGOCYCLIC FATIGUE OR OLIGOCYCLIC AND POLYCYCLIC FATIGUE TEST RIG

TECHNICAL FIELD

The present invention relates to a low-cycle, and optionally combined low-cycle and high-cycle, fatigue test rig, for reproducing bearing of turbine engine parts, such as at least one blade root bearing against a recess contact surface of a rotor disc.

PRIOR ART

A turbine engine rotor disc comprises, on the periphery thereof, an annular array of recesses into which blade roots are fitted, which are for example of the dovetail type, to form a rotor wheel. During operation, the blades are subjected to centrifugal forces, and the roots thereof bear against lateral contact surfaces of the recesses in the disc. The blades are further subjected to oscillations related to the aerodynamic forces which cause relative sliding between the blade roots and the disc. Said loads affect the service life of the blade-disc attachments.

The analysis of the service life of the blade-disc attachments is based on calculations which are made complex by the effect of contact on the calculated stresses and service lives. The calculation for predicting service lives is possible by means of a complete digital model. The difficulty of the model put in place lies in the input data required. The model requires a correlation between a stress range experienced under the blade-disc contact and the number of cycles for initiating a corresponding crack.

In view of this analysis, it is necessary to devise a test which is capable of reproducing, in laboratory conditions, blade-disc contact which is subjected to low-cycle fatigue (LCF) or combined low-cycle and high-cycle fatigue (HCF) loading. A test rig should make it possible to determine, by means of experiment, the service life of the blade-disc contact. This experimental data will subsequently be used to set the digital methodologies for determining service life on the actual parts for which it is impossible to determine a service life by means of experiment.

In the current art, low-cycle fatigue test rigs each comprise a support member which is fixed to a frame and defines at least one bearing surface, and a test piece which is connected to traction means for loading the test piece so that it bears against the or each bearing surface of the member.

However, said test rigs are not completely satisfactory in particular because the homogeneity of the contact between the parts is not guaranteed at the start of the test and for the entire duration of the test, and this can distort the calculations for assessing the service life. In addition, the support member and the test piece are relatively bulky in said test rigs. Furthermore, it can be difficult to equip said test rigs with measuring and control instruments, and to have easy access to said instruments. Lastly, said test rigs do not always permit very representative assessments with respect to the industrial application of the parts.

The aim of the present invention is in particular to provide a simple, effective and economical solution to at least some of the above-mentioned problems.

SUMMARY OF THE INVENTION

The invention proposes a low-cycle, and optionally combined low-cycle and high-cycle, fatigue test rig, for reproducing bearing of turbine engine parts, such as at least one blade root bearing against a recess contact surface of a rotor disc, said test rig comprising a support member which is fixed to a frame and defines at least one bearing surface, and a test piece which is connected to traction means for loading the test piece so that it bears against the or each bearing surface of the member, characterised in that the or each bearing surface is supported by an element which is mounted so as to rotate about a first axis on the support member, and in that the test piece is connected to the traction means by means for articulation around a second axis which is substantially perpendicular to the first axis, and in that it further comprises means for adjusting and locking the element and the test piece in positions around the above-mentioned axes.

According to the invention, the element has a degree of freedom with respect to the support member, and the test piece has a degree of freedom with respect to the traction means. This double degree of freedom is particularly advantageous because the relative positions of the test piece and of the element supported by the support member can be adjusted precisely so as to ensure that the test piece does in fact bear against the or each bearing surface of the support member. Once the test piece and the element are correctly positioned, they are locked in these positions so that they maintain said positions at the start of the test. The invention thus ensures perfectly homogeneous contact at the start of the test.

The test rig according to the invention can be adapted to the known technology, since the frame and the traction means can be those used in the prior art.

The element preferably comprises a substantially cylindrical outer surface which cooperates with a surface which is substantially complementary to the support member to guide the element in rotation about the first axis.

The means for locking the element and/or the test piece are for example of the screw type.

The means for locking the element can comprise at least one screw which is screwed into a threaded hole in the element and which passes through an aperture in the support member, the head of the screw being intended, when the screw is tightened, to rest against the support member so as to fix the element in place, and the aperture having a substantially elongate shape so as to allow an angular displacement of the element about the first axis when the screw is inserted in the hole in the element but is not tightened.

Advantageously, the element is supported by a middle portion of the member which is connected by at least a first arm to a base which is fixed to the frame, said first arm being inclined in such a way that it is oriented substantially perpendicularly to a bearing surface of the element. Therefore, the first arm is substantially collinear with or tangential to the shearing forces applied to the bearing surface defined by the element. This makes it possible to limit the risks of deformation of the support member during a test.

The middle portion can be connected by at least a second arm to a cross bar which is substantially parallel to the base, said second arm being inclined in such a way that it is substantially parallel to a normal to the bearing surface defined by the element. The second arm is thus substantially parallel to the normal forces applied to the bearing surface of the element. This also makes it possible to limit the risks of deformation of the support member during a test, and considerably reduces the risk of misalignment of the contact of the parts. The invention thus makes it possible to maintain the contact of the parts for the entire duration of the test.

The support member can comprise two elements which are mounted so as to rotate on two middle portions of the member, respectively, and about first axes which are parallel to and at a distance from one another, said elements comprising bearing surfaces which are intended to reproduce portions of two adjacent blade roots of a rotor wheel. In other words, the test rig makes it possible to reproduce two blade-disc contacts.

In one embodiment of the invention, the middle portions of the member are each connected to two parallel cross bars by two second arms, respectively, the cross bars, the first and second arms, the middle portions and the base of the member being formed in one piece, and the test piece passing between the cross bars in the assembled position.

During a high-cycle fatigue test, the support member can be connected to the frame by an I-shaped part having a flexible middle portion, and the test piece can be connected to one end of a vibrating blade, the other end of which is connected to the traction means by another I-shaped part having a flexible middle portion, such that the test piece and the support member are supported in a region located in the region of a vibration knot of a first vibration mode of the rig.

This position of the bearing region makes it possible to ensure maximum sliding of the parts in the region of the contact whilst limiting the movements of the assembly. This makes it possible to equip the test rig with a plurality of instruments and in particular with a camera for viewing the bearing region.

DESCRIPTION OF THE DRAWINGS

The invention will be better understood, and other details, features and advantages of the invention will become apparent upon reading the following description, given by way of non-limiting example and with reference to the accompanying drawings, in which:

FIG. 1 is a very schematic view of the attachment of a blade root in a recess in a rotor disc of a turbine engine, FIG. 2 is a partial schematic perspective view of a low-cycle fatigue test rig according to the invention and shows the test piece and the support member of said rig, FIG. 3 is a half view of the support member and the test piece from FIG. 2, FIG. 8 is a schematic perspective view of a low-cycle and high-cycle fatigue test rig according to the invention, and FIG. 9 is a diagram showing the position of the bearing region between the test piece and the support member, with respect to a first vibration mode of the rig.

DETAILED DESCRIPTION

Figure 4:
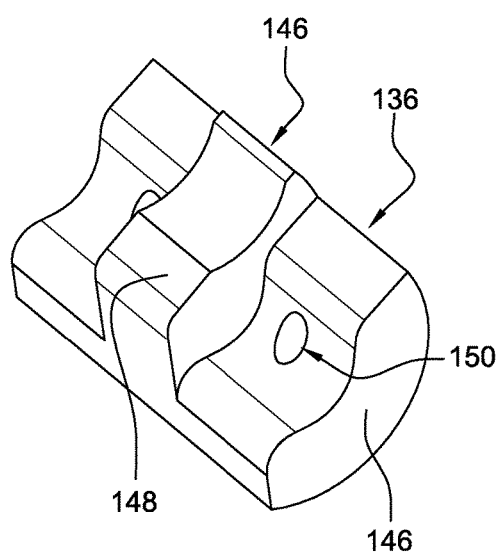
FIG. 4 is a schematic perspective view of one of the elements supported by the support member from FIG. 2.
Figure 5:
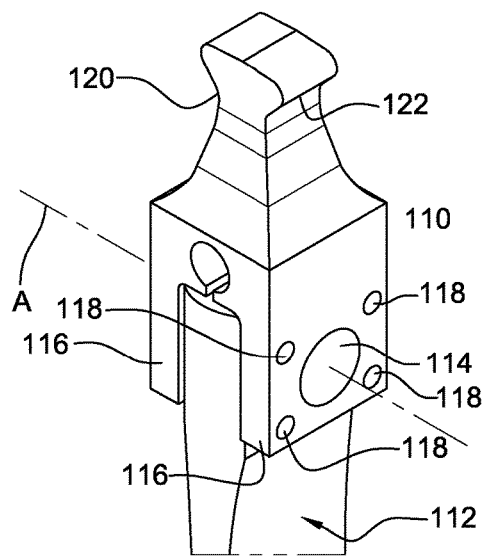
FIG. 5 is a schematic perspective view of the test piece from FIG. 2.

Reference is firstly made to FIG. 1, which schematically shows a blade-disc attachment of a turbine engine, the blade 10 comprising a root 12 which is inserted in a recess 14 in the periphery of a rotor disc 16, said disc comprising an annular array of recesses 14 of this type for receiving blade roots. The assembly formed by the disc 16 and the blades 10 form a rotor wheel of the turbine engine. In this case, the root 12 is of the dovetail type. Two adjacent recesses 14 in the disc 16 are separated from one another by a tooth 15, the teeth 15 located on either side of the root 12 of the blade from FIG. 1 being shown in part.

During operation, the blade 10 is subjected to centrifugal forces (arrow 18) and the vane thereof has a tendency to oscillate (arrow 20), causing the lateral portions of the blade root 12 to bear and slide against lateral contact surfaces of the recess 14 in the disc. The arrows 24 show normal forces which are applied to the surfaces facing the blade root 12 and the recess 14, and the arrows 26 denote shearing forces which are applied to said surfaces.

FIGS. 2 to 7 show an embodiment of the test rig according to the invention, which is designed to reproduce two blade-disc contacts which are subjected to low-cycle fatigue (LCF) and combined low-cycle and high-cycle fatigue (HCF) loading, in order to determine, by means of experiment, the service life of said contacts.

The test rig 100 comprises substantially two portions, a first portion 102 which is connected to traction means 104 and which is intended to reproduce a tooth of a rotor disc, and a second portion 106 which is connected to a fixed frame 108 and is intended to reproduce portions of two blade roots engaging with said tooth.

The first portion 102 comprises a test piece 110 which is mounted at the end of a blade 112, the other end of which is connected to the traction means 104. Said traction means 104 comprise for example an actuator, the free end of the rod of which is connected to the blade 112, and the cylinder of which is supported by a fixed portion of the test rig. Said actuator is preferably oriented in parallel with the blade 112 in such a way that the traction force is parallel to the longitudinal axis of the blade 112.

The test piece 110 is articulated on a shaft 114 which is supported by the end of the blade 112 so as to be able to rotate the test piece about an axis A which is substantially perpendicular to the longitudinal axis of the blade 112 and is parallel to the plane of the drawing in FIG. 3. In the example shown in FIG. 5, the test piece 110 comprises a U-shaped base comprising two parallel legs 116 which are at a distance from one another, a flat end of the blade 112 being inserted between said legs and supporting the shaft 114, the ends of which are accommodated and slide in rotation in holes in the legs 116. The test piece 110 can rotate about the axis A over an angular range of approximately a few tens of degrees.

At least one of the legs 116 of the test piece 110 comprises threaded through-holes 118 for mounting screws (not shown) for preventing the test piece 110 from rotating. The free ends of said screws are intended to rest against the end of the blade 112 and to fix the test piece 110 in place in a predetermined position around the axis A.

Figure 6:
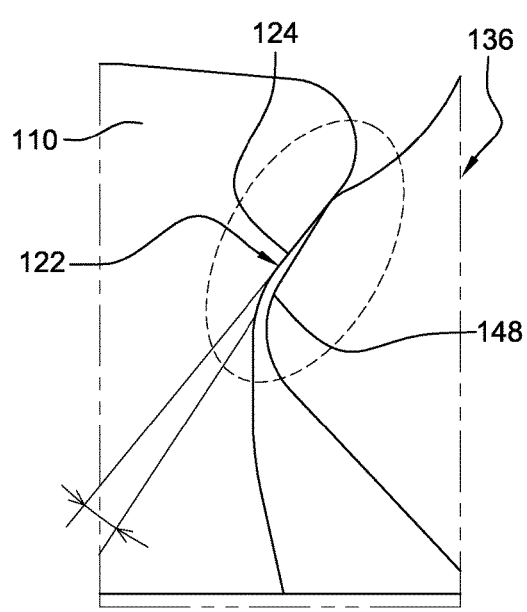
FIG. 6 is a very schematic view of the bearing region between the test piece and the one of the elements of the support member from FIG. 2.

The test piece 110 further comprises a portion which is shaped into a disc tooth and is connected to the above-mentioned base, said portion reproducing portions of two adjacent recesses in the disc. Said portion has a general dovetail shape and comprises two lateral faces which are shaped to reproduce the contact surfaces 120, 122 of two adjacent recesses in the disc. Each of said contact surfaces 120, 122 comprises a relatively planar bearing surface 124 (FIG. 6).

The second portion 106 of the test rig 100 comprises a support member 126 comprising a base 128 which is fixed to the frame 108 and two cross bars 130 which are parallel to one another and to the base and are at a distance from one another, said bars 130 being connected to the base by arms 132, 134 which support bearing elements 136 of the test piece 110.

The base 128 has a parallelepiped shape and is preferably fixed in a flat manner in a horizontal position on the frame 108. Said base is connected by two opposite ends to lower ends of first arms 132, the upper ends of which are connected to middle portions 138 for supporting bearing elements 136, said middle portions 138 being connected to the lower ends of second arms 134, the upper ends of which are connected to the ends of the cross bars 130.

In the example shown, each middle portion 138 is a cylindrical portion and comprises an inner cylindrical surface portion 140 which is oriented towards the inside of the member 126 and an outer cylindrical surface portion 142 which is oriented towards the outside of the member.

There are two first arms 132 or lower arms, each arm 132 connecting an end of the base 128 to a lower end of the middle portion 138. As will be explained in greater detail in the following, said arms 132 are inclined, in particular with respect to the base 128.

There are four second arms 134 or upper arms, each middle portion 138 being connected by a pair of second arms 134 to first ends of the cross bars 130, the opposite ends of which are connected by the other pair of second arms 134 to the other middle portion 138. The second arms 134 of each pair are parallel to and at a distance from one another, each cross bar 130 and the second arms 134 which are connected to said bar being located substantially in the same plane. Said arms 134 are inclined with respect to the base 128 and to the bars 130.

The elements 136 are mounted so as to be rotatable on the inner cylindrical surfaces 140 of the middle portions 138 around parallel axes B, respectively, said axes B being substantially perpendicular to the axis A, that is to say substantially perpendicular to the plane of the drawing in FIG. 3.

Each element 136, which can more easily be seen in FIG. 4, comprises a substantially cylindrical outer surface 144 which is complementary to the above-mentioned inner surface 140 of the corresponding middle portion 138, in such a way that the element 136 can slide in rotation about the axis B with respect to the member. Each element 136 further comprises a bearing pad 146 comprising a planar surface 148 for bearing against one of the above-mentioned surfaces 124 of the test piece 110. The position of each element 136 around the corresponding axis B can be adjusted and locked by means of screws (not shown) which are screwed into threaded holes 150 in the element. Said screws are intended to pass through apertures 152 in the middle portions 138 of the member, which have an elongate shape, the elongation axis of which is substantially perpendicular to the axes B. The screws are inserted from the outside of the member into the apertures and the threaded holes in the elements, the heads of the screws being intended to rest against the outer surfaces 142 of the middle portions 138 in order to hold the elements 136.

In the assembled position shown in FIGS. 2 and 3, the test piece 110 extends between the cross bars 130 of the member 126 in such a way that the blade 112 extends in an opposite direction to the base. The surfaces 124 of the test piece 110 are intended to bear against the surfaces 148 of the elements 136.

As can be seen in FIG. 6, when assembled, said surfaces 124, 148 can be separated from one another by a small amount of play and can be slightly inclined with respect to the other to the extent that they cannot come into complete contact with one another.

This drawback is overcome by means of the two degrees of freedom around the axes A and B of the test piece 110 and the elements 136, respectively, which make it possible to precisely adjust the relative positions of the test piece and the elements and to ensure that the bearing surfaces 124, 148 are indeed in contact with one another at the start of a test. Once said positions have been adjusted, they are locked by means of the above-mentioned screws.

Figure 7:
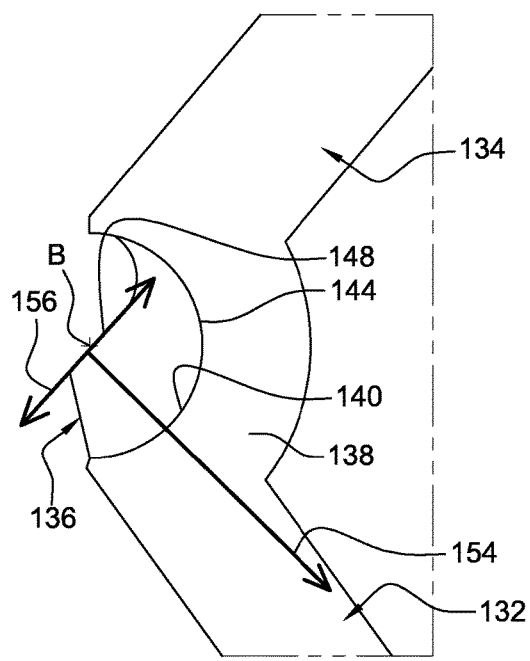
FIG. 7 is a very schematic view of portion of the support member and shows inclined arms of said member.

As can be seen in FIG. 7, each first arm 132 is substantially parallel to the normal forces (arrow 154) applied to the surface 148 of the corresponding element 136, and each second arm 134 is substantially parallel to the shearing forces (arrows 156) applied to said surfaces. This makes it possible to limit the deformations of the member in use and ensures that the contact between the elements and the test piece is maintained for the entire duration of a test.

FIG. 8 shows a variant of the test rig 200 according to the invention, which is designed in this case to reproduce two blade-disc contacts which are subjected to low-cycle fatigue (LCF) and high-cycle fatigue (HCF) loading.

The test rig 200 has all the above-mentioned features of the rig 100, and additionally the following features.

The member 126 is fixed to the frame by means of an I-shaped part 158. Said part 158 comprises two parallel, substantially parallelepipedal, solid blocks 160 which are interconnected by a flexible wall 162 which is perpendicular to the blocks. The base 128 of the member 126 is applied and fixed to one of the blocks 160, the second block being fixed to the frame 108.

The blade 112 is fixed to the traction means by means of another I-shaped part 164, which is substantially identical to the first 160. One of the blocks 166 of said part 164 is fixed to one end of the blade 112 (opposite the test piece 110) and the other block 166 is connected to the traction means. The flexible walls 162, 168 of the I-shaped parts are substantially coplanar.

The test rig 200 comprises an excitation means, such as a shaker, which bears against the I-shaped part 164 which is connected to the blade 112, for example in the region of the block 166 which is connected to said blade, to make the blade 112 vibrate.

FIG. 9 schematically shows the test rig 200 and a first vibration mode 170 of the rig. Advantageously, as shown in this drawing, the bearing surfaces of the test piece 110 and the elements 136 which are supported by the member 126 are located in the region of a vibration knot 172 of this first mode, so as to excite the blade 112 with a high amplitude, and to maximise the relative movements (sliding) between the test piece and the member whilst limiting the movements of the assembly formed by the test piece 110 and the member 126.

The invention claimed is:

1. A low-cycle, and/or high-cycle, fatigue test rig, for reproducing bearing of turbine engine parts, the test rig comprising:
    a frame;
    a support member which is fixed to the frame and defines at least one bearing surface; and
    a traction element, wherein a test piece is connected to the traction element for loading the test piece so that the test piece bears against the at least one bearing surface, wherein the at least one bearing surface is supported by a support element which is mounted so as to rotate about a first axis on the support member, and wherein the test piece is connected to the traction element for articulation around a second axis which is perpendicular to the first axis, wherein support element comprises a locking element configured to provide selective adjustment and locking of the support element and the test piece in positions around the first and second axes.

2. The test rig according to claim 1, wherein the support element comprises:
    a cylindrical outer surface which cooperates with
    a surface which is complementary to the support member to guide the support element in rotation about the first axis.

3. The test rig according to claim 1, wherein the locking element is a threaded fastener.

4. The test rig according to claim 3, wherein the locking element comprises:
    at least one screw which is screwed into
    a threaded hole within the support element and which passes through
    an aperture in the support member, the head of the screw resting against the support member so as to fix the element in place when the screw is tightened, and the aperture having a elongate shape so as to allow an angular displacement of the support element about the first axis when the screw is inserted in the hole within the element but is not tightened.

5. The test rig according to claim 1, wherein the support element is supported by
    a middle portion of the support member that is connected by at least
    a first arm to a
    base that is fixed to the frame, the first arm being inclined to be oriented perpendicularly to the at least one bearing surface defined by the support element.

6. The test rig according to claim 5, wherein the middle portion is connected by
    at least a second arm to
    a cross bar which is parallel to the base, the second arm being inclined to be parallel to the at least one bearing surface defined by the support element.

7. The test rig according to claim 5, wherein the support member comprises
    two elements that are mounted to rotate on two middle portions of the support member, respectively, and about first axes that are parallel to and at a distance from one another, the elements comprising bearing surfaces intended to reproduce portions of two adjacent blade roots of a rotor wheel.

8. The test rig according to claim 7, wherein the middle portions of the support member are each connected to
    two parallel cross bars by
    two second arms, respectively, the cross bars, the first and second arms, the middle portions and the base of the support member being formed in one piece, and the test piece passing between the cross bars in an assembled position.

9. The test rig according to claim 1, wherein the support member is connected to the frame by
    an I-shaped part having a flexible middle portion, and the test piece is connected to one end of
    a vibrating blade, the other end of which is connected to the traction element by
    another I-shaped part having a flexible middle portion, wherein the test piece and the support member are supported in a region located in the region of a vibration knot of a first vibration mode during a high-cycle fatigue test.

10. The test rig according to claim 1, wherein at least one blade root is bearing against a recess contact surface of a rotor disc.

* * * * *